United States Patent [19]

Gardner et al.

[11] Patent Number: 4,469,697
[45] Date of Patent: Sep. 4, 1984

[54] PENTACYCLIC COMPOUNDS, THEIR PHARMACEUTICAL COMPOSITIONS, AND METHODS OF USE

[75] Inventors: Derek V. Gardner, Bishops Stortford; Trevor J. White, Buntingford, both of England

[73] Assignee: Beecham Group p.l.c., Brentford, England

[21] Appl. No.: 479,016

[22] Filed: Mar. 25, 1983

[30] Foreign Application Priority Data

Mar. 27, 1982 [GB] United Kingdom ............... 8209087
Mar. 30, 1982 [GB] United Kingdom ............... 8209298
Apr. 27, 1982 [GB] United Kingdom ............... 8212154

[51] Int. Cl.³ ............... A61K 31/55; C07D 487/14
[52] U.S. Cl. ............... 424/250; 260/239.3 P; 260/243.3; 260/244.4; 544/342
[58] Field of Search ............... 260/239.3 P, 243.3, 260/244.4; 544/342; 424/250

[56] References Cited

U.S. PATENT DOCUMENTS 3,354,041 10/1970 Van der Burg et al. ............ 544/343
3,701,778 10/1972 Van der Burg ..................... 544/343

FOREIGN PATENT DOCUMENTS 1173783 12/1969 United Kingdom ............... 544/343
1229252 4/1971 United Kingdom ............... 544/343
1229253 4/1971 United Kingdom ............... 549/12

OTHER PUBLICATIONS

S. Ogren et al., "Reevaluation of the Indoleamine Hypothesis of Depression. Evidence for a Reduction of Functional Activity of Central 5-HT Systems by Antidepressant Drugs," *J. Neural. Trans.*, 46, pp. 85–103, (1979).

L. Stein et al., "Effects of Benzodiazepines on Cental Serotonergic Mechanisms," *Advances in Biochemical Psychopharmacology*, vol. 14, pp. 29–44, (Raven Press, New York City, 1975).

Primary Examiner—Robert T. Bond
Attorney, Agent, or Firm—James F. Haley, Jr.; Susan H. Rauch

[57] ABSTRACT

Compounds of formula (I), and pharmaceutically acceptable salts thereof:

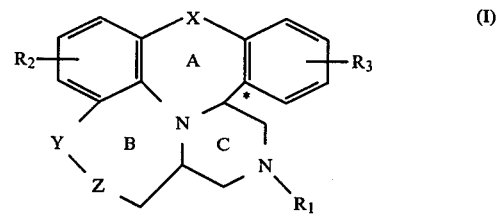

(I)

wherein:

X is $CH_2$, O, S or $NR_4$ wherein $R_4$ is hydrogen or $C_{1-4}$ alkyl;

one of Y and Z is $NR_5$ and the other is $CR_6R_7$ wherein $R_5$ is hydrogen, $C_{1-4}$ alkyl or $C_{1-4}$ acyl and $R_6$ and $R_7$ are either both hydrogen or together form an oxo group;

$R_1$ is hydrogen, $C_{1-6}$ alkyl, $C_{3-7}$ cycloalkyl, $C_{4-7}$ cycloalkenyl or $C_{1-4}$ alkyl substituted by $C_{2-7}$ alkenyl, $C_{2-7}$ alkynyl, $C_{3-7}$ cycloalkyl, amino optionally substituted by one or two $C_{1-4}$ alkyl or by $C_{4-6}$ polymethylene optionally containing an oxygen atom or by phenyl $C_{1-4}$ alkyl optionally substituted in the phenyl ring by $C_{1-4}$ alkyl, $C_{1-4}$ alkoxy, halogen or trifluoromethyl; and $R_2$ and $R_3$ are the same or different and are hydrogen, halogen, hydroxy, $C_{1-4}$ alkyl $C_{1-4}$ alkoxy or trifluoromethyl having pharmacological activity, a process for their preparation and their pharmaceutical use.

14 Claims, No Drawings

PENTACYCLIC COMPOUNDS, THEIR PHARMACEUTICAL COMPOSITIONS, AND METHODS OF USE

This invention relates to pentacyclic compounds having mood modifying, particularly anti-depressant and anxiolytic, activity, to pharmaceutical compositions containing them and to processes for their preparation.

U.K. Pat. No. 1173 783 discloses compounds of formula (A):

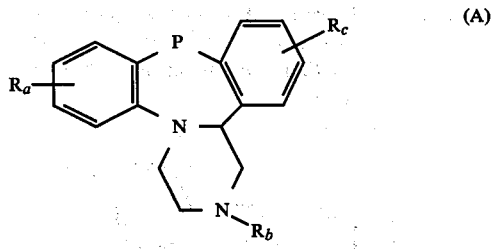

wherein:

$R_a$ and $R_c$ each represents a hydrogen or halogen atom, a hydroxy, lower acyloxy, alkyl or alkoxy group, or a trifluoromethyl group;

$R_b$ represents hydrogen, a lower alkyl or aralkyl group, an aminoethyl or aminopropyl group N-substituted by one or more lower alkyl groups, or a lower alkyl group forming a substituent of an N-containing heterocyclic ring, the said ring being directly bonded to the nitrogen atom of the piperazine ring, and P represents a single bond, a methylene, ethylene or —CH=CH— group.

U.K. Pat. No. 1229252 discloses compounds of formula (B):

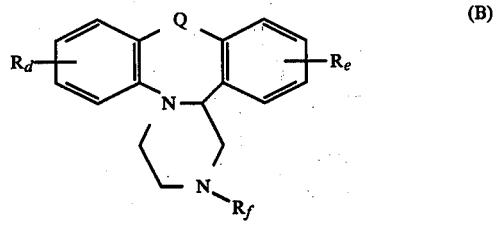

wherein:

$R_d$ and $R_e$ represents hydrogen or halogen or hydroxy acyloxy, alkoxy or alkyl having 1-6 carbon atoms, or trifluoromethyl groups;

$R_f$ represents hydrogen, an alkyl group having 1-6 carbon atoms, an aralkyl group with 7-12 carbon atoms, an aminoethyl or aminopropyl group which, if desired, can be N-substituted by an alkyl group with 1-6 carbon atoms, or an alkyl group having 1-6 carbon atoms and a nitrogen-containing heterocyclic ring; and Q represents oxygen, sulphur or

with $R_g$ representing an alkyl group having 1-6 carbon atoms.

A structurally distinct class of compounds has now been discovered and found to have mood-modifying activity. In particular, such compounds have been found to inhibit the behavioural symptoms induced by the administration of 5-methoxy-N,N-dimethyl tryptamine to mice and are therefore central 5-hydroxytryptamine antagonists. The compounds consequently possess anti-depressant and anxiolytic activity.

Accordingly, the present invention provides a compound of formula (I), or a pharmaceutically acceptable salt thereof:

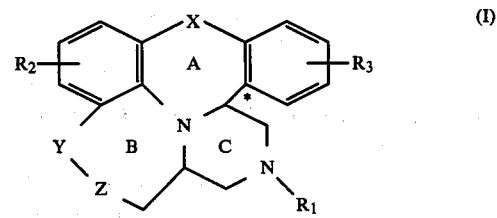

wherein:

X is $CH_2$, O, S or $NR_4$ wherein $R_4$ is hydrogen or $C_{1-4}$ alkyl;

one of Y and Z is $NR_5$ and the other is $CR_6R_7$ wherein $R_5$ is hydrogen, $C_{1-4}$ alkyl or $C_{1-4}$ acyl and $R_6$ and $R_7$ are either both hydrogen or together form an oxo group;

$R_1$ is hydrogen, $C_{1-6}$ alkyl, $C_{3-7}$ cycloalkyl, $C_{4-7}$ cycloalkenyl or $C_{1-4}$ alkyl substituted by $C_{2-7}$ alkenyl, $C_{2-7}$ alkynyl, $C_{3-7}$ cycloalkyl, amino optionally substituted by one or two $C_{1-4}$ alkyl groups or by $C_{4-6}$ polymethylene optionally containing an oxygen atom or by phenyl $C_{1-4}$ alkyl optionally substituted in the phenyl ring by $C_{1-4}$ alkyl, $C_{1-4}$ alkoxy, halogen or trifluoromethyl; and $R_2$ and $R_3$ are the same or different and are hydrogen, halogen, hydroxy, $C_{1-4}$ alkyl, $C_{1-4}$ alkoxy or trifluoromethyl.

When X is $NR_4$, suitable examples of $R_4$ include hydrogen, methyl or ethyl, preferably methyl. X is preferably $CH_2$.

Within Y and Z, suitable examples of $R_5$ include hydrogen, methyl, ethyl, n- and iso-propyl and n-, and sec-butyl. Preferably $R_5$ is hydrogen. Often Y is $NR_5$ and Z is $CR_6R_7$ as defined.

Suitable examples of $R_1$ when $C_{1-6}$ alkyl include methyl, ethyl, n- and iso-propyl and n-, and sec-butyl.

When $R_1$ is $C_{1-4}$ alkyl substituted by phenyl optionally substituted as hereinbefore defined, examples of such optional substituents include methyl, ethyl, methoxy, ethoxy, fluoro, chloro, bromo or trifluoromethyl. Preferably, phenyl is unsubstituted.

When $R_1$ is $C_{1-4}$ alkyl substituted by amino optionally substituted as hereinbefore defined, examples of such optional substituents include methyl and ethyl and, together with the nitrogen atom, piperidino and morpholino.

Preferably, $R_1$ is hydrogen or $C_{1-4}$ alkyl, such as methyl and ethyl.

Suitable examples for $R_2$ and $R_3$ include hydrogen, hydroxy, methyl, ethyl, methoxy, ethoxy, bromo, chloro, fluoro and trifluoromethyl. Most preferably $R_2$ and $R_3$ are both hydrogen.

There is a class of compounds within formula (I) wherein Y is $NR_5$ as defined and Z is $CR_6R_7$ as defined, $R_1$ is hydrogen or $C_{1-6}$ alkyl and the remaining variables are as defined in formula (I).

There is a preferred class of compounds within formula (I) of formula (II), or a pharmaceutially acceptable salt thereof:

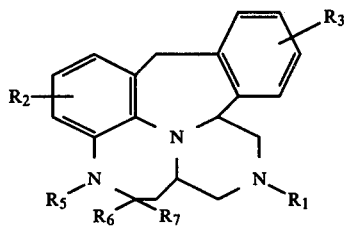
(II)

wherein $R_1$, $R_2$, $R_3$, $R_5$, $R_6$ and $R_7$ are as defined in formula (I).

Suitable and preferred values for $R_1$, $R_2$, $R_3$, $R_5$, $R_6$ and $R_7$ are as described in relation to formula (I).

There is a sub-class of compounds within formula (II) of formula (III), or a pharmaceutically acceptable salt thereof:

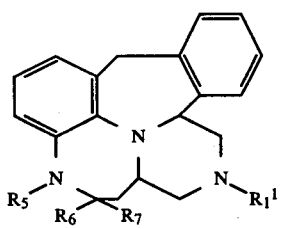
(III)

wherein $R_1{}^1$ is hydrogen or $C_{1-4}$ alkyl and $R_5$, $R_6$ and $R_7$ are as defined in formula (I).

Suitable and preferred values for $R_1{}^1$, $R_5$, $R_6$ and $R_7$ are as described for the corresponding variables in formula (I).

There is a preferred sub-class of compounds within formula (III) of formula (IV), or a pharmaceutically acceptable salt thereof:

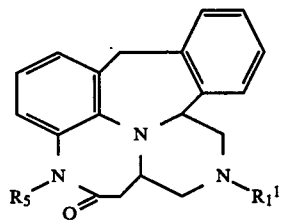
(IV)

wherein $R_1{}^1$ and $R_5$ are as defined in formula (III). Suitable and preferred values for $R_1{}^1$ and $R_5$ are as described for the corresponding variables in formula (I).

Within the definition of formula (IV), there is 13-methyl-1,3,7,11b,12,13,14,14a-octahydro-2H-3,13,14b-triaza-tribenzo[b,ef,kl]heptalen-2-one and pharmaceutically acceptable salts thereof.

There is a further preferred sub-class of compounds within formula (III) of formula (V) or a pharmaceutically acceptable salt thereof:

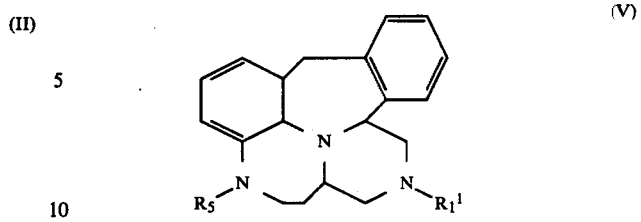
(V)

wherein $R_1{}^1$ and $R_5$ are as defined in formula (III). Suitable and preferred values for $R_1{}^1$ and $R_5$ are as described for the corresponding variables in formula (I).

There is a further class of compounds within formula (I) of formula (VI):

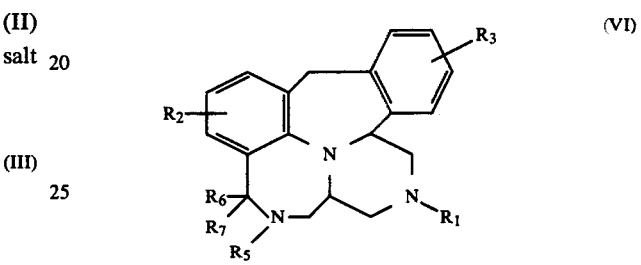
(VI)

wherein $R_1$, $R_2$, $R_3$, $R_5$, $R_6$ and $R_7$ are as defined in formula (I).

Suitable and preferred values for $R_1$, $R_2$, $R_3$, $R_5$, $R_6$ and $R_7$ are as described in relation to formula (I).

There is a favourable sub-class of compounds within formula (VI) of formula (VII):

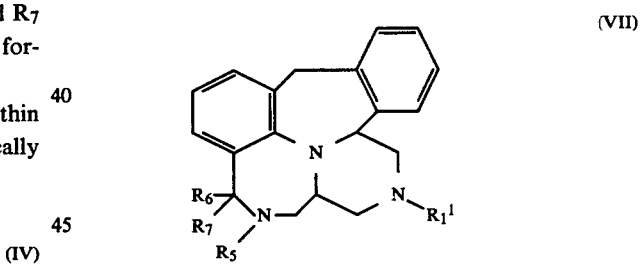
(VII)

wherein $R_1{}^1$, $R_5$, $R_6$ and $R_7$ are as defined in formula (III).

Suitable and preferred values for $R_1{}^1$, $R_5$, $R_6$ and $R_7$ are as described for the corresponding variables in formula (I).

There is a preferred sub-class of compounds within formula (VI) of formula (VIII):

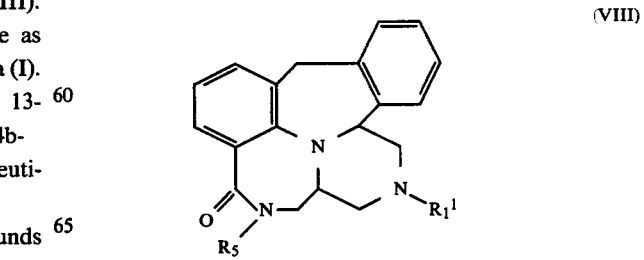
(VIII)

wherein $R_1{}^1$ and $R_5$ are as defined in formula (III).

Suitable and preferred values for $R_1{}^1$ and $R_5$ are as described for the corresponding variables in formula (I).

There are further classes and sub-classes of compounds within formula (I) corresponding to formulae (II) to (VII) respectively but wherein the X=CH$_2$ group is replaced by $X^1$ wherein $X^1$ is oxygen or sulphur.

A compound of formula (I) has a number of asymmetric centres (indicated by '*' in formula (I)) and is thus capable of existing in stereoisomeric forms. The present invention extends to each of these forms individually and to mixtures of such stereoisomers including racemates. In addition, the ring systems A, B and C of a compound of formula (I) may exist in a number of conformations.

Again the present invention extends to all combinations of ring conformations individually and in mixtures. However, the most preferred compounds of the present invention are those identified as Series A and B hereinafter.

A pharmaceutically acceptable salt of a compound of formula (I) includes an acid addition salt of any of the nitrogen atoms referred to in formula (I) and of any nitrogen-containing substituent for $R_1$, the acid addition salt being derived from a pharmaceutically acceptable inorganic or organic acid, such as hydrochloric acid, hydrobromic acid, sulphuric acid, maleic acid and acetic acid.

The present invention also provides a process for the preparation of a compound of formula (I) or a pharmaceutically acceptable salt thereof which process comprises the reaction of a compound of formula (IX):

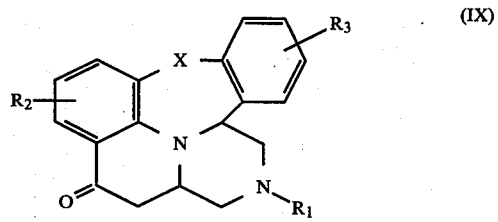

with a compound of formula (X):

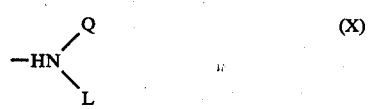

wherein Q is hydrogen and L is a leaving group (when Y is NR$_5$) or Q is N$_2$ and L is absent and treating with an acidic reagent, hydrolysing the resulting intermediate and thereafter optionally reducing an R$_6$/R$_7$ oxo group, converting an R$_5$ hydrogen to other R$_5$, converting an R$_1$, R$_2$ or R$_3$ group to R$_1$ or other R$_2$ or R$_3$ and/or forming a pharmaceutically acceptable salt thereof.

Examples of the leaving group L include any of those customarily employed in Beckmann rearrangements. Suitable examples include C$_{1-4}$ alkoxy, such as methoxy, tosyloxy, phosphate and hydroxy. Preferably L is hydroxy.

The reaction with H$_2$NL is carried out in an inert solvent, such as an alkanol e.g. ethanol in the presence of a base, such as sodium hydroxide. Usually the reaction takes place at elevated temperatures, preferably under reflux.

To produce a compound of formula (I), the intermediate of formula (XI) hereinafter depicted undergoes a Beckmann rearrangement in the presence of the acidic reagent. Beckmann rearrangements are well known in the art and any acidic reagent suitable for catalysing such rearrangements may be used in the present invention. Examples of such reagents include sulphuric acid, phosphorus pentoxide, sulphur trioxide, sulphonyl chloride, boron trifluoride, phosphorus pentachloride and, preferably, polyphosphoric acid. The reaction is conveniently carried out at an elevated temperature, for example a temperature within the range 40° to 200° C., or 90° to 170° C.

The reaction with HN$_3$ i.e. Q is N$_2$, L is absent is normally carried out in the presence of an acid catalyst at low temperatures. Any acid catalyst customarily used in Schmidt reactions is suitable, such as sulphuric, hydrochloric, trichloracetic or polyphosphoric acid. Suitable inert solvents include benzene, chloroform, ethanol or dioxan. The hydrazoic acid may be used as such or it may be generated in situ from sodium azide in the acidic medium.

The Schmidt rearrangement with HN$_3$ is non-sterospecific and produces a mixture of products of formula (I) wherein Y is NH and Z is CO and where Y is CO and Z is NH. The products may be separated by conventional methods, such as by chromatography.

The Beckmann rearrangement is stereospecific according to the stereochemistry of the intermediate oxime and therefore produces compounds of formula (I) wherein Y is NH and Z is CO.

The invention therefore provides a process for the preparation of compounds of formula (I) wherein Y is NR$_5$ and Z is CR$_6$R$_7$ which process comprises reacting a compound of formula (XI):

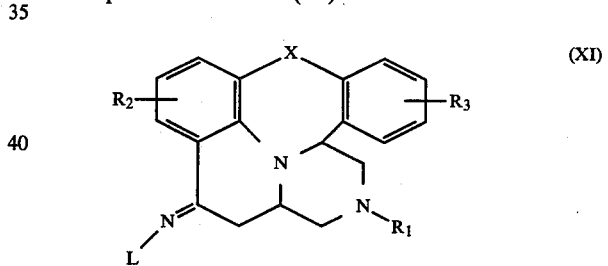

wherein $R_1$, $R_2$, $R_3$ and L are as hereinbefore defined, with an acidic reagent, hydrolysing the resulting intermediate and thereafter optionally reducing an R$_6$/R$_7$ oxo group, converting an R$_5$ hydrogen to another R$_5$ group, converting an R$_1$, R$_2$ or R$_3$ group to another R$_1$, R$_2$ or R$_3$ group and/or forming a pharmaceutically acceptable salt thereof.

The R$_6$/R$_7$ oxo group may be reduced using conventional strong reducing agents, such as lithium aluminium hydride or diborane in tetrahydrofuran or ether. The invention therefore provides a process for the preparation of a compound of formula (I) wherein R$_6$ and R$_7$ are both hydrogen, which process comprises reducing a compound of formula (I) wherein R$_6$ and R$_7$ together form an oxo group.

An important sub-class of an optional conversion of R$_1$ are those in which a compound of formula (I), wherein R$_1$ is hydrogen, is converted into another compound of formula (I), wherein R$_1$ is as follows:

(a) wherein R$_1$ is C$_{1-6}$ alkyl, by alkylation with a C$_{1-6}$ alkyl halide in a solvent, such as acetone, in the presence of a base;

(b) wherein $R_1$ is $C_{3-7}$ cycloalkenyl, by reaction with a $C_{3-7}$ cycloalkenyl halide, such as a $C_{3-7}$ cycloalkenyl bromide, when the halide atom is allylic;

(c) wherein $R_1$ is $C_{1-6}$ alkyl substituted by $C_{2-7}$ alkenyl or $C_{2-7}$ alkynyl, by reaction with a $C_{2-11}$ alkenyl or $C_{2-11}$ alkynyl halide, such as a $C_{2-11}$ alkenyl or $C_{2-11}$ alkynyl bromide, in a solvent, such as acetone, in the presence of a base, such as potassium carbonate;

(d) wherein $R_1$ is $C_{1-4}$ alkyl substituted by amino optionally substituted by one or two $C_{1-4}$ alkyl groups or by $C_{4-6}$ polymethylene optionally containing an oxygen atom by reaction with a compound of formula (XII):

$$L_4-(CH_2)_r-NR_9R_{10} \qquad (XII)$$

in which r is 1 to 4, $R_9$ and $R_{10}$ are hydrogen or $C_{1-4}$ alkyl or together are $C_{4-6}$ polymethylene optionally containing an oxygen atom, $L_4$ is a leaving group, such as chloro, and r is as hereinbefore defined, in a solvent, such as acetone, in the presence of a base.

(e) wherein $R_1$ is $C_{1-4}$ alkyl substituted by phenyl being optionally substituted by $C_{1-4}$ alkyl, $C_{1-4}$ alkoxy, halogen or trifluoromethyl, by reaction with the correspondingly substituted $C_{1-4}$ alkyl halide, such as the bromide.

Compounds of the formula (I) wherein $R_1$ is hydrogen are most suitably prepared via the compound of formula (I) wherein $R_1$ is benzyl by conventional hydrogenolysis.

The present invention extends to all of the above conversions, whether singly or in combination.

When $R_1$ in formula (I) is a functional group that may possibly interfere with the course of the reaction or that may not possibly survive it, then it is preferred to carry out the preparation of a compound of formula (I) with $R_1$ as hydrogen or benzyl and subsequently to convert the hydrogen atom into the desired group for $R_1$ by, for example, one or more of the conversions described hereinbefore.

Suitable $R_5$ hydrogen conversions are as hereinbefore described for (a) under $R_1$ hydrogen conversions.

An example of an optional conversion of $R_2$ or $R_3$ in a compound of formula (I) into another $R_2$ or $R_3$ is the conversion of $C_{1-4}$ alkoxy into hydroxy using, for example, aqueous hydrobromic acid.

The optional formation of a pharmaceutically acceptable acid addition salt of a compound of formula (I) may be carried out by simple reaction of a compound of formula (I) with a pharmaceutically acceptable acid.

Compounds of formula (IX) may be prepared by cyclising, in the presence of a dehydrating agent, a compound of formula (XIII):

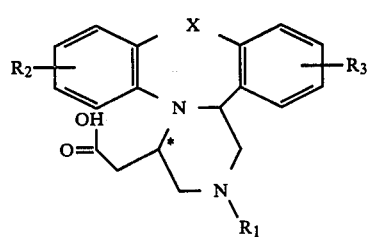

(XIII)

wherein $R_1$, $R_2$, $R_3$ and X are as hereinbefore defined.

The cyclisation reaction is normally carried out under acid conditions, for example in methanesulphonic acid, at room temperature. Any conventional dehydrating agent may be used although phosphorus pentoxide is preferred.

A compound of formula (XIII) may be prepared by hydrolysis of a compound of formula (XIV):

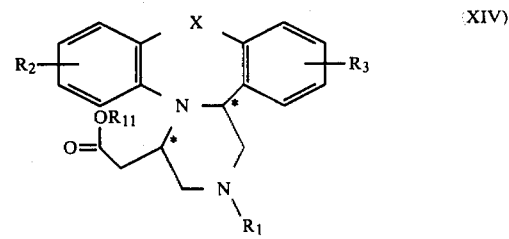

(XIV)

wherein $R_{11}$ is $C_{1-4}$ alkyl, especially methyl, and $R_1$, $R_2$, $R_3$ and X are as hereinbefore defined, which in turn may be prepared by cyclisation of a compound of formula (XV):

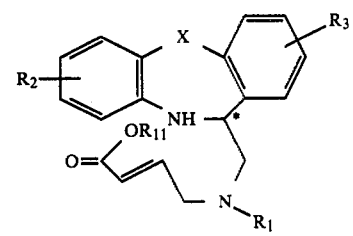

(XV)

wherein $R_1$, $R_2$, $R_3$, $R_{11}$ and X are as hereinbefore defined.

Because of the asymmetric centres indicated by '*' in formulae (XIV) and (XV), the compounds can exist in two diastereoisomers or as a mixture of both. One diastereoisomer of formula (XIV), herein referred to as Series A, can be prepared by carrying out the cyclisation of a compound of formula (XV) under an atmosphere of nitrogen at a temperature of 150° C. and then carrying out the hydrolysis of the Series A diastereoisomer of formula (XIV) thus obtained in 5M hydrochloric acid at reflux temperature.

Alternatively, a mixture of the two diastereoisomers of formula (XIV) can be prepared by carrying out the cyclisation of a compound of formula (XV) in methanesulphonic acid at room temperature, separating the Series B isomer from the resulting mixture of Series A and Series B isomers, and then carrying out the hydrolysis of the Series B isomer of formula (XIV) in 10% sodium hydroxide solution at reflux temperature. Separation of the Series B isomer is achieved by conventional techniques, such as column chromatography.

A compound of formula (XV) can be prepared from a compound of formula (XVI):

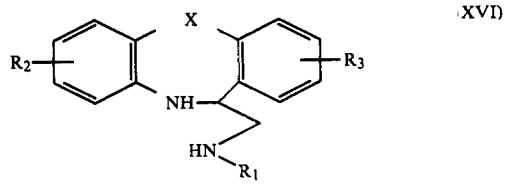

(XVI)

wherein $R_1$, $R_2$, $R_3$ and X are as hereinbefore defined by reaction with a compound of formula (XVII):

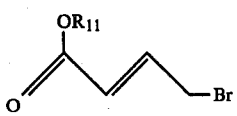

wherein $R_{11}$ is as previously defined, in the presence of potassium carbonate in dimethylformamide.

Compounds of formula (XVII) are known compounds and can readily be prepared by methods known in the literature.

Compounds of formula (XVI) are also known known compounds, or structurally similar to known compounds, and can be prepared by the process described in U.K. Pat. Nos. 1173783 and 1229253 or U.S. Pat. Nos. 3,534,041 and 3,701,778 or by an analogous process thereto.

The present invention also provides a pharmaceutical composition, which comprises a compound of formula (I), or pharmaceutically acceptable salt thereof, and a pharmaceutically acceptable carrier.

A pharmaceutical composition of the invention, which may be prepared by a mixture, is usually adapted for oral or parenteral administration and, as such, may be in the form of tablets, capsules, oral liquid preparations, powders, granules, lozenges, reconstitutable powders, or injectable or infusable solutions or suspensions. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colourants.

For parenteral administration, fluid unit dosage forms are prepared utilising a compound of the invention, or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. Parenteral suspensions are prepared in substantially the same manner, except that the compound is suspended in the vehicle instead of being dissolved and sterilised by exposure to ethylene oxide before suspension in a sterile vehicle. Advantageously, a surfactant or wetting agent is included in the composition to facilitate uniform distribution of the compound.

The dose of the compound used in the treatment of CNS disorders, such as depression or anxiety will vary in the usual way with the seriousness of the disorders, the weight of the sufferer, and other similar factors. However, as a general guide suitable unit doses may be 0.05 to 10.0 mg/kg for example 0.2 to 1 mg/kg and such unit doses may be administered more than once a day, for example two or three times a day, so that the total daily dosage is in the range of about 0.01 to 10 mg/kg; and such therapy may extend for a number of weeks or months.

The invention also provides a method of treatment of CNS disorders, in particular depression in mammals including humans, which comprises administering to the sufferer an anti-depressant effective amount of a compound of the invention, or pharmaceutically acceptable salt thereof.

The invention further provides a compound or pharmaceutically acceptable salt thereof, for use in the treatment of CNS disorders, in particular depression.

The following Examples illustrate the preparation of the compounds of the invention. The following Descriptions illustrate the preparation of intermediates to the compounds of the present invention. All temperatures are in degrees celsius.

DESCRIPTION 1

Methyl-4-(methylaminomethyl-5,6-dihydro-6-morphanthridinyl)but-2-enoate

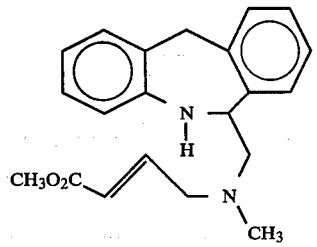

6-methylaminomethyl-5,6-dihydromorphanthridine (20 g, 0.084 mol) was dissolved in dry dimethylformamide (150 ml). To this solution, potassium carbonate (11.6 g, 0.084 mol) was added and to the resulting mixture stirred at room temperature, methyl-4-bromocrotonate (85%, 17.6 g, 0.084 mol) was added dropwise. The reaction mixture was stirred at room temperature for 4 hours (the reaction followed by t.l.c. on silica gel eluted with diethyl ether). When t.l.c. indicated that the reaction was complete, the solvent was removed and ether (100 ml)/water (200 ml) added to the residue. The organic layer was separated and the aqueous fraction further extracted with 2×50 ml portions of ether. The organic extracts were combined, dried (MgSO$_4$) and the solvent removed in vacuo to give a brown oil. Purification of the product was achieved by filtration through a short column of silica gel eluted with ether. The title product was obtained as a brown oil in 65% yield.

DESCRIPTION 2a (a) 4-Carbomethoxymethyl-2-methyl-1,2,3,4,10-14b-hexahydropyrazino[1,2-f]morphanthridine (Series 'B')

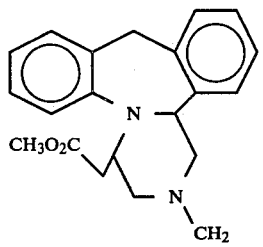

Methyl-4-(methylaminomethyl-5,6-dihydro-6-morphanthridinyl)but-2-enoate (1.5 g) (description 1) was dissolved in methanesulphonic acid (20 ml) and the resulting solution stirred at room temperature for 1 hour. The reaction mixture was poured onto ice/water basified with sodium hydroxide and extracted with ethyl acetate (3×25 ml). Removal of the solvent in vacuo gave a brown oil which was purified by column chromatography on silica gel eluted with ether.

0.25 g (35%) of ester diastereoisomer A was isolated.
0.78 g (52%) of ester diastereoisomer B was isolated.
Ester B was converted to the hydrochloride salt and recrystallized from methanol/ether to give white crystals mp 231°–234° C.

| Analysis $C_{21}H_{25}N_2O_2Cl$ | | |
|---|---|---|
| | Required | Found |
| N | 7.52 | 7.47 |
| C | 67.65 | 67.40 |
| H | 6.71 | 6.86 |
| Cl | 9.53 | 9.31 |

DESCRIPTION 2b

4-Carboxymethyl-2-methyl-1,2,3,4,10,14b-hexahydropyrazino[1,2-f]morphanthridine hydrochloride (Series 'B')

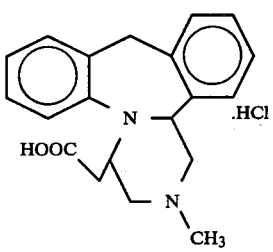

The ester (series B) prepared in (a) (5 g) was heated under reflux in 10% sodium hydroxide for 2 hours. The reaction mixture was then acidified with 5N hydrochloric acid. As the solution cooled the hydrochloride salt of the acid precipitated as a white solid. The solid was filtered, washed with water and dried in a vacuum oven. After drying the yield was 85%, mp 295°–299° C.

| | C | H | N |
|---|---|---|---|
| Found | 66.78 | 6.13 | 7.72 |
| $C_{20}H_{23}N_2O_2Cl$ requires | 66.95 | 6.42 | 7.81 |

DESCRIPTION 3

12-Methyl-1,2,6,10b,11,12,13,13a-octahydro-12,13b-diazabenzo[g,h]pleiadene-2-one (Series 'B') (D3)

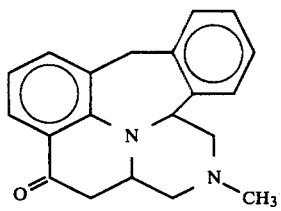

The acid (series B) prepared in 2b (9.5 g, (31.25 mmol) was dissolved in methanesulphonic acid (95 g) and phosphorus pentoxide (19 g, 0.14 mol) was added in portions, with cooling. The reaction mixture was stirred at room temperature for 3 days then poured onto ice/water, basified with sodium hydroxide and extracted with ethyl acetate (3×250 ml). The organic extracts were combined, washed with water (3×250 ml) dried (MgSO$_4$.H$_2$O) and the solvent removed in vacuo and the crude ketone was obtained as an off white foam. Column chromatography on silica gel eluted with ether together with increasing proportion of ethyl acetate, gave the title compound as a white foam in 53% yield. This was converted to the maleate salt and recrystallised from methanol ether, m.p. 176°–9° C.

| Analysis $C_{24}H_{24}N_2O_5$ | | |
|---|---|---|
| | Required | Found |
| C | 68.57 | 68.47 |
| N | 6.66 | 6.57 |
| H | 5.71 | 5.58 |

DESCRIPTION 4

12-Methyl-1,2,6,10b,11,12,13,13a-octahydro-12,13b-diazabenzo[gh]pleiadene-2-one oxime (Series 'B')

(D4)

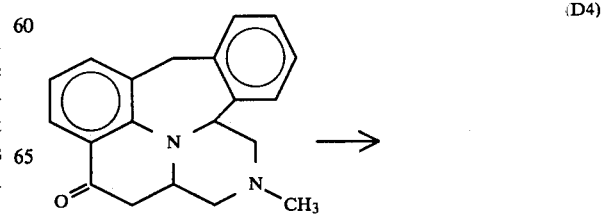

-continued

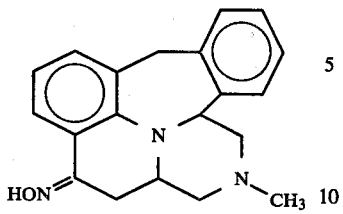

To a mixture of ketone (1 g, 0.0032 mol), hydroxylamine hydrochloride (0.35 g, 0.005 mol), ethanol (2 ml) and water (0.5 ml) was added sodium hydroxide (0.65 g, 0.016 mol) in portions. The resulting mixture was refluxed for 10 mins and then extracted with ethyl acetate. The product, purified by column chromatography on silica gel eluted with ether, was obtained as a white solid in 58% yield mp 216°–219° C.

A sample was converted to the maleate salt and after recrystallisation from acetone/ether had melting point 164°–166° C.

Mass spectrum m/e 319.

| Analysis | Calc. | Found |
|---|---|---|
| C | 66.20 | 65.43 |
| H | 5.75 | 6.06 |
| N | 9.65 | 8.94 |

DESCRIPTION 5

(a)

4-Carbomethoxymethyl-2-methyl-1,2,3,4,10,14b-hexahydropyrazino[1,2-f]morphanthridine hydrochloride (Series 'A') (D5)

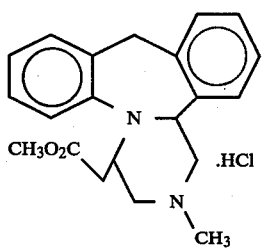

(D5)

The Series 'A' ester was prepared from the butenoate of Description 1 by heating under an atmosphere of nitrogen at a temperature of 150° in a manner similar to that in Description 2a, and converted into a hydrochloride salt, m.p. 259°–262°.

| | C | H | N | Cl |
|---|---|---|---|---|
| Found | 67.44 | 6.66 | 7.41 | 9.32 |
| $C_{21}H_{25}N_2O_2Cl$ requires | 67.65 | 6.71 | 7.52 | 9.53 |

DESCRIPTION 5(b)

4-Carboxymethyl-2-methyl-1,2,3,4,10,14b-hexahydropyrazino[1,2-f]morphanthridine hydrochloride (Series 'A') (D5(b))

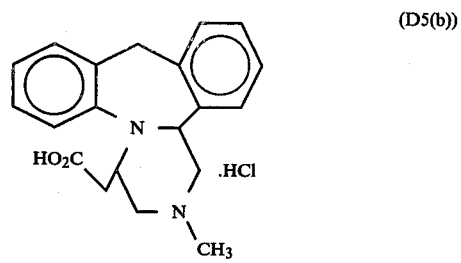

(D5(b))

The title compound was prepared in a manner similar to that outlined in Description 2b, m.p., 268°–270°.

| | C | H | N | Cl |
|---|---|---|---|---|
| Found | 66.35 | 6.43 | 7.64 | 9.73 |
| $C_{20}H_{23}N_2O_2Cl$ requires | 66.81 | 6.42 | 7.81 | 9.90 |

DESCRIPTION 6

12-Methyl-1,2,6,10b,11,12,13,13a-octahydro-12,13b-diazabenzo[g,h]pleiadene-2-one (Series 'A') (D6)

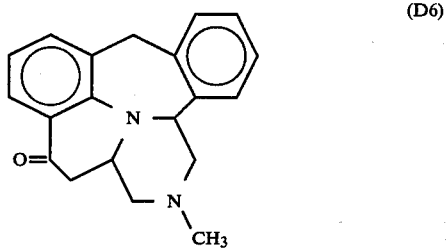

(D6)

The title compound was prepared from the acid of Description 5b in a similar manner to that outlined in Description 3 and converted into a hydrochloride salt, m.p. 289°–291°.

| Found: | $M^+$ 304.1581 |
|---|---|
| $C_{20}H_{20}N_2O$ requires: | 304.1576 |

DESCRIPTION 7

12-Methyl-1,2,6,10b,11,12,13,13a-octahydro-12,13b-diazabenzo[gh]pleiadene-2-one oxime (Series 'A') (D7)

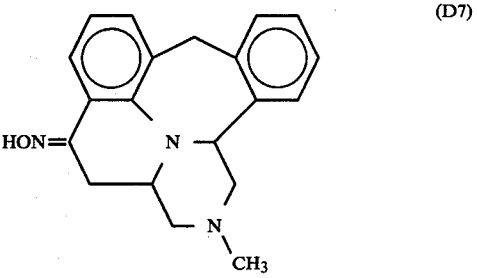

(D7)

The title compound was prepared from the ketone of Description 6 in a manner analogous to the procedure outlined in Description 4. m.p. 209°–210°.

|   | C | H | N |
|---|---|---|---|
| Found | 66.29 | 5.80 | 9.60 |
| $C_{20}H_{21}N_3O$ requires | 66.20 | 5.79 | 9.65 |

DESCRIPTION 8

12-Methyl-1,2,10b,11,12,13,13a-hexahydro-2H-6-oxa-12,13b-diaza-benzo[gh]pleiadene-2-one (D8)

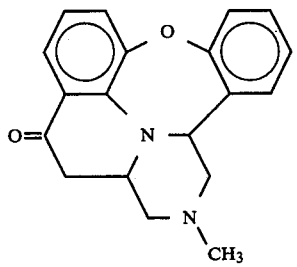

(D8)

The title compound was prepared in a manner similar to that in Description 3. A sample was converted into the monomaleate salt and recrystallised from acetone/ether m.p. 187°–188° C.

|   | C | H | N |
|---|---|---|---|
| Found | 65.10 | 5.11 | 6.53 |
| $C_{23}H_{22}N_2O_6$ Requires | 65.40 | 5.21 | 6.64 |
| Found |   | M+ 306.1362 |   |
| $C_{19}H_{18}N_2O_2$ requires |   | 306.1368 |   |

DESCRIPTION 9

12-Methyl-1,2,10b,11,12,13,13a-hexahydro-2H-6-thia-12,13b-diaza-benzo[gh]pleiadene-2-one (D9)

(D9)

The title compound was prepared in a manner similar to that in Description 3. A sample was converted into a maleate salt, m.p. 178°–180° (from acetone-ether).

|   | C | H | N |
|---|---|---|---|
| Found | 62.90 | 5.03 | 6.31 |
| $C_{20}H_{22}N_2O_5S$ Requires | 63.01 | 5.02 | 6.39 |

DESCRIPTION 10

12-Methyl-1,2,10b,11,12,13,13a-hexahydro-2H-6-oxa-12,-3b-diaza-benzo[gh]pleiadene-2-one oxime (D10)

(D10)

The title compound was prepared in a manner similar to that in Description 4. A sample was converted into a monomaleate salt m.p. 146°–149° C.

|   | C | H | N |
|---|---|---|---|
| Found | 62.71 | 5.20 | 9.59 |
| $C_{23}H_{23}N_3O_6$ requires | 63.15 | 5.30 | 9.60 |

HPLC purity by area >99%

EXAMPLE 1

13-Methyl-1,3,7,11b,12,13,14,14a-Octahydro-2H-3,13,14b-triaza-tribenzo[b,ef,kl]heptalen-2-one (Series 'B')

(E1)

The oxime (0.45 g; 1.4 m.mol) was heated in excess polyphosphoric acid at 130°–140° C. for 20 min. The mixture was poured onto ice/water, basified with 40% sodium hydroxide, and extraction with ethyl acetate removed the crude product. Chromatography on silica with ethyl acetate containing increasing amounts of ethanol gave the lactam as a white solid in 47% yield. The lactam was converted into a monomaleate salt and recrystallised from acetone/diethyl ether m.p. 199°–202° C.

| Analysis as hydrate $C_{24}H_{27}N_3O_6$ | | |
|---|---|---|
| | Required | Found |
| C. | 63.58 | 63.68  64.06 |
| H. | 5.96 | 5.59  5.64 |
| N. | 9.27 | 9.09  9.18 |

Mass spectrum m/e 319
HPLC purity by area % >99.9%

EXAMPLE 2

13-Methyl-1,3,7,11b,12,13,14,14a-octahydro-2H-3,13,14b-triaza-tribenzo[b,ef,kl]heptalen-2-one (Series 'A') (E2)

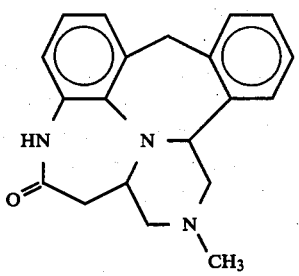

(E2)

The title compound was prepared from the Series 'A' oxime of Description 7 by a Beckmann rearrangement with phosphorus pentachloride. m.p. 165°–168°.

| Found | $M^+$ 319.1674 |
|---|---|
| $C_{20}H_{21}N_3O$ requires | 319.1684 |

EXAMPLE 3

13-Methyl-1,2,7,11b,12,13,14,14a-octahydro-3H-3,13,14b-triaza-tribenzo[b,ef,kl]heptalene (E3)

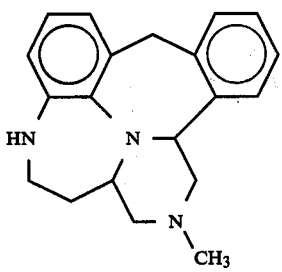

(E3)

The amide prepared in Example 1 (0.8 g, 0.0025 mol) was dissolved in dry tetrahydrofuran (40 ml) and excess lithium aluminium hydride added in portions. The reaction mixture was stirred at reflux for 30 mins after which time tlc (silica gel/ethyl acetate) indicated no starting material remained. Water was then carefully added and the product extracted with ethyl acetate. Column chromatography on silica, using as eluant ethyl acetate containing increasing amounts of methanol, gave the required amine in 92% yield. A sample of the amine was converted into a monomaleate salt and recrystallised from acetone m.p. 139°–142° C.

| | C | H | N |
|---|---|---|---|
| Found | 67.05 | 6.41 | 9.56 |
| $C_{24}H_{27}N_3O_4.\frac{1}{2}H_2O$ requires | 66.97 | 6.51 | 9.76 |
| Found: | $M^+$ 305.1896 | | |
| $C_{20}H_{23}N_3$ requires | 305.1892 | | |

HPLC: Purity by area >99%.

Nmr: (CDCl$_3$): δ: 1.64 (1H; d,d,d,d; J=15, 6.5, 1, 1; 1 eq CH). 1.92 (1H; d,d,d,d; 1 ax CH), 2.09 (1H; d,d; J=10, 10; 14 ax CH), 2.30 (3H, s, NCH$_3$), 2.44 (1H; d,d; J=11, 11; 12 ax CH), 2.70 (1H; d,d,d; J=11,2,2; 12 eq CH), 2.80 (1H, s, ex D$_2$O NH), 2.83 (1H; d,d,d; J=10, 1.5, 1.5; 14 eq CH); 3.18 (1H; d,d,d; J=10,7,1; 2 eq CH), 3.26 (1H, d, J=12.5, 7-bridgehead CH), 3.27 (1H; d,d,d; J=10.5, 10.5, 6.5; 2 ax CH), 4.02 (1H; d,d,d,br; J=10,10,2,0.5; 14a-CH), 4.55 (1H; d,d; J=10.5, 3; 11b-CH), 4.68 (1H, d, J=12.5, 7-bridgehead CH), 6.54–7.13 (7H,m, aromatic CH).

EXAMPLE 4

3,13-Dimethyl-1,2,7,11b,12,13,14,14a,octahydro-3H-3,13,14b-triaza-tribenzo[b,ef,kl]heptalene (E4)

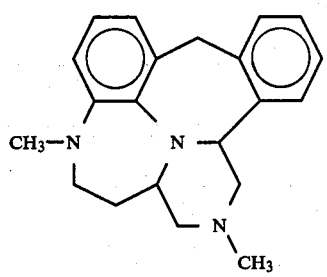

(E4)

The amine prepared in Example 3 (0.3 g 0.00098 mol) was dissolved in acetonitrile (18 ml) and formaldehyde (0.78 ml, 0.0096 mol, 37–41% solution) added. The pH was adjusted to 4 using ethereal hydrogen chloride. Sodium cyanoborohydride (0.186 g, 0.0029 mol) was then added and the pH maintained at 4 for 2 hours. After this time the pH was lowered to ~1 and the mixture stirred for 30 mins. The solvent was removed and the product partitioned between ethyl acetate and water the organic phase was separated, dried (MgSO$_4$) and evaporated to dryness. Column chromatography on silica gel eluted with ethyl acetate gave the required compound in 70% yield. A sample was converted to the monomaleate salt and recrystallised from acetone/ether m.p. 102°–105° C.

| Found | $M^+$ 319.2042 |
|---|---|
| $C_{21}H_{25}N_3$ requires | 319.2048 |

HPLC purity by area 99%

EXAMPLE 5

3-Acetyl-13-methyl-1,2,7,11b,12,13,14,14a-octahydro 3H-3,13,14b-triaza-tribenzo[b,ef,kl]heptalene (E5)

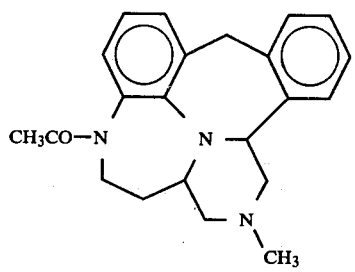

(E5)

The amine prepared in Example 3 (0.3 g, 0.00098 mol) was dissolved in dichloromethane (10 ml) and potassium carbonate (0.168 g, 0.0012 mol) added. To this stirred mixture was added acetic anhydride (0.119 g, 0.11 ml, 0.0011 mol) and the mixture stirred at room temperature for 3 hours when tlc (silica gel/ethyl acetate) showed rection was complete. Water was added and the product extracted into dichloromethane. Chromatography on silica using ethyl acetate as eluant gave the title compound (0.28 g; 82%). This was converted to the monomaleate salt and recrystallised from acetone m.p. 193°–195° C.

| Found | M+ 347.2007 |
|---|---|
| C$_{22}$H$_{25}$N$_3$O requires | 347.1997 |

HPLC purity by area 99.9%

EXAMPLE 6

13-Methyl-1,2,7,11b,12,13,14,14a-octahydro-3H-2,13,14b-triaza-tribenzo[b,ef,kl]heptalen-3-one (E6)

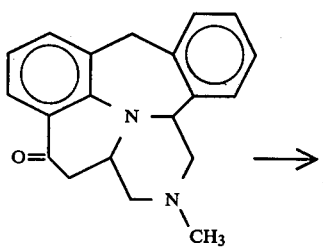
→
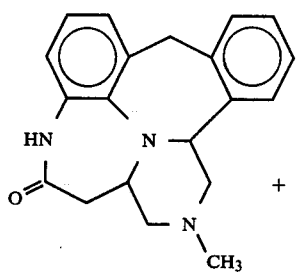
+

Example 1

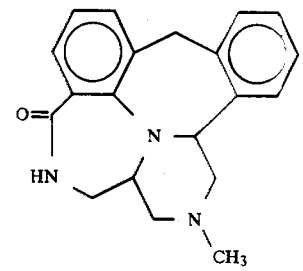

Example 6

The ketone prepared in Description 3 (2 g, 0.0066 mol) was dissolved in chloroform (10 ml) and the reaction mixture cooled to 0° C. in an ice-bath. Concentrated sulphuric acid (5 ml) was then added followed by the portionwise addition of sodium azide (0.5 g, 0.0077 mol). The reaction mixture was stirred at 0° C. for 2½ hours, basified with sodium hydroxide and the products extracted into ethyl acetate. Column chromatography on silica using ethyl acetate containing increasing amounts of methanol gave:

(a)

13-Methyl-1,3,7,11b,12,13,14,14a-octahydro-2H-3,13,14b-triaza-tribenzo[b,ef,kl]-heptalen-2-one (Series 'B')

0.49 g (23%) as prepared previously in Example 1.

and (b)

13-Methyl-1,3,7,11b,12,13,14,14a-octahydro-2H-2,13,14b-triaza-tribenzo[b,ef,kl]-heptalen-3-one (Series 'B')

1.1 g (53%) a portion of which was converted into a monomaleate salt and recrystallised from acetone/ether m.p. 210°–213° C.

EXAMPLE 7

13-Methyl-1,2,3,11b,12,13,14,14a-octahydro-7-oxa-3,13,14b-triaza-tribenzo[b,ef,kl]heptalen-2-one (E7)

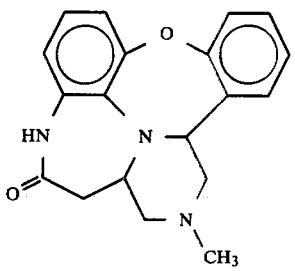

(E7)

The title compound was prepared in a manner similar to that described in Example 6.

| Found | M+ 321.1483 |
|---|---|
| C$_{19}$H$_{19}$N$_3$O$_2$ requires | 321.1477 |

EXAMPLE 8

13-Methyl-1,2,7,11b,12,13,14,14a-octahydro-7-oxa-2,13,14b-triaza-tribenzo[b,ef,kl]heptalen-3-one (E8)

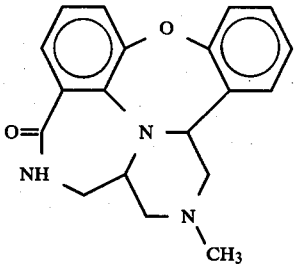

(E8)

The title compound was prepared in a manner similar to that described in Example 6, a sample was converted to the monomaleate salt m.p. 251°–253° C.

|  | C | H | N |
|---|---|---|---|
| Found (monomaleate salt) | 71.07 | 6.04 | 13.11 |
| $C_{23}H_{23}N_3O_6$ requires | 71.01 | 5.96 | 13.07 |
| Found | $M^+$ 321.1490 | | |
| $C_{19}H_{19}N_3O_2$ | 321.1477 | | |
| Found: | $M^+$ 319.1694 | | |
| $C_{20}H_{21}N_3O$ requires | 319.1685 | | |

HPLC purity by area 97%.

EXAMPLE 9

13-Methyl-1,2,3,11b,12,13,14,14a-octahydro-7-thia-3,13,14b-triaza-tribenzo[b,ef,kl]heptalen-2-one (E9)

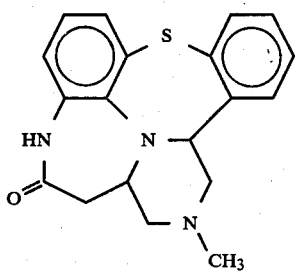

(E9)

The title compound was prepared in a manner similar to that described in Example 6.

| Found | $M^+$ 337.1259 |
|---|---|
| $C_{19}H_{19}N_3OS$ requires | 337.1249 |

EXAMPLE 10

13-Methyl-1,2,3,11b,12,13,14,14a-octahydro-7-thia-2,13,14b triaza-tribenzo[b,ef,kl]heptalen-3-one (E10)

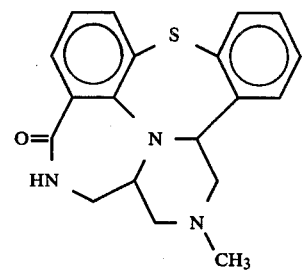

(E10)

The above compound was prepared in a similar manner to the method described in Example 6.

| Found | $M^+$ 337.1238 |
|---|---|
| $C_{19}H_{19}N_3OS$ requires | 337.1249 |

EXAMPLE 11

13-Methyl-1,2,3,11b,12,13,14,14a-octahydro-7-oxa-3,13,14b-triaza-tribenzo[b,ef,kl]heptalene (E11)

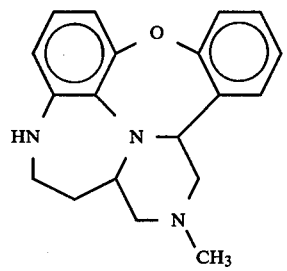

(E11)

The title compound was prepared in a manner similar to that described in Example 3.

| Found | $M^+$ 307.1677 |
|---|---|
| $C_{19}H_{21}N_3O$ requires | 307.1684 |

EXAMPLE 12

13-Methyl-1,2,3,11b,12,13,14,14a-octahydro-7-oxa-2,13,14b-triaza-tribenzo[b,ef,kl]heptalene (E12)

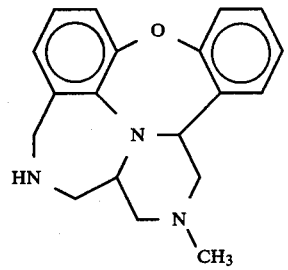

(E12)

The title compound was prepared in a manner similar to that described in Example 3.

| Found | M+ 307.1680 |
|---|---|
| C₁₉H₂₁N₃O requires | 307.1684 |

EXAMPLE 13

13-Methyl-2,3,7,11b,12,13,14,14a-octahydro-1H-2,13,14b-triaza-tribenzo[b,ef,kl]heptalane (E13)

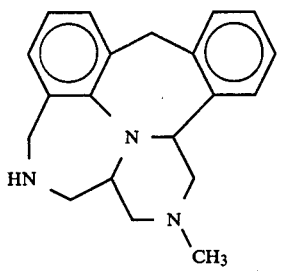
(E13)

The title compound was prepared in a manner similar to that in Example 3 from the amide prepared in Example 6.

| Found | M+ 305.1893 |
|---|---|
| C₂₀H₂₃N₃ requires | 305.1892 |

PHARMACOLOGY

Compounds of the invention inhibit the behavioural symptoms induced by 5-methoxy-N,N-dimethyltryptamine (5-MDMT), a central 5-hydroxytryptamine agonist, and are central 5HT antagonists. As such they would be expected to possess antidepressant (Ogren, S O, Fuxe, K, Agnati, L F, Gustafsson J A, Jonsson, G, and Holm A C, 1979, J Neural Trans, 46, 85–103) and/or anxiolytic (Stein, L, Kline, D, and Belluzzi, J D, 1975, in Advances in Biochemical Psychopharmacology, ed Costa, E, and Greengard, P, Vol 14, 29–44, Raven Press, NY) activity.

METHOD

Mice (♂ CD-1 Charles River) are pretreated with the compounds (10 animals/group) under investigation and 1 h later are injected with 10 mg/kg i.p. 5-methoxy-N,N-dimethyltryptamine (Sigma). The symptoms of fore-paw tapping movements, head jerks and splayed limbs are scored: 1, present; 0, absent, giving a maximum score of 3/mouse or 30/group. Results are expressed as the percentage inhibition compared to the group treated with 5-methoxy-N,N-dimethyltryptamine alone. The dose of compound inhibiting the symptoms by 50% is determined graphically.

The results are shown in Table 1.

TOXICITY

No toxic effects were observed in the above tests.

TABLE 1

| Compound | ED₅₀ mg/kg (p.o.) |
|---|---|
| 13-Methyl-1,3,7,11b,12,13,14,14a-octahydro-2H—3,13,14b-triaza-tribenzo[b,ef,kl]heptalen-2-one (Series B) (Example 1) | 3.0 |
| 3,13-Dimethyl-1,2,7,11b,12,13,14,14a-octahydro-3H—3,13,14b-triaza-tribenzo[b,ef,kl]heptalene (Series B) (Example 4) | 1.1 |
| 13-Methyl-1,2,7,11b,12,13,14,14a-octahydro-2H—2,13,14b-triaza-tribenzo[b,ef,kl]heptalen-3-one (Series B) (Example 6) | 8.0 |

We claim:

1. A compound of formula (I), or a pharmaceutically acceptable salt thereof:

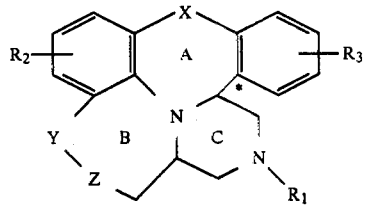
(I)

wherein:

X is CH₂, O, S or NR₄ wherein R₄ is hydrogen or C₁₋₄ alkyl;

One of Y and Z is NR₅ and the other is CR₆R₇ wherein R₅ is hydrogen, C₁₋₄ alkyl or carboxylic C₁₋₄ acyl and R₆ and R₇ are either both hydrogen or together form an oxo group;

R₁ is hydrogen, C₁₋₆ alkyl, C₃₋₇ cycloalkyl, C₄₋₇ cycloalkenyl or C₁₋₄ alkyl substituted by C₂₋₇ alkenyl, C₂₋₇ alkynyl, C₃₋₇ cycloalkyl, amino optionally substituted by one or two C₁₋₄ alkyl groups, disubstituted by C₄₋₆ polymethylene optionally interrupted in the methylene chain by an oxygen atom, or substituted by phenyl C₁₋₄ alkyl optionally substituted in the phenyl ring by C₁₋₄ alkyl, C₁₋₄ alkoxy, halogen or trifluoromethyl;

R₂ and R₃ are the same or different and are hydrogen, halogen, hydroxy, C₁₋₄ alkyl, C₁₋₄ alkoxy or trifluoromethyl.

2. A compound according to claim 1 of formula (III) or a pharmaceutically acceptable salt thereof:

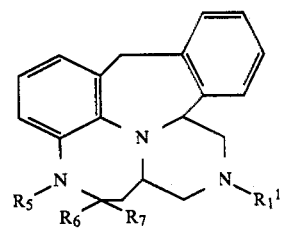
(III)

wherein R₁¹ is hydrogen or C₁₋₄ alkyl and R₅, R₆ and R₇ are as defined in claim 1.

3. A compound according to claim 2 of formula (IV) or a pharmaceutically acceptable salt thereof:

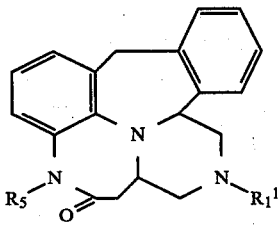

(IV)

wherein R₁¹ and R₅ are as defined in claim 2.

4. 13-Methyl-1,3,7,11b,12,13,14,14a-octahydro-2H-3,13,14b-triaza-tribenzo[b,ef,kl]heptalen-2-one.

5. A compound according to claim 2 of formula (V) or a pharmaceutically acceptable salt thereof:

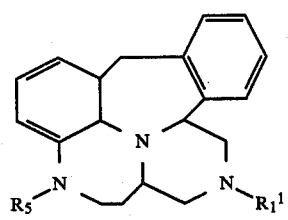

(V)

wherein R₁¹ and R₅ are as defined in claim 2.

6. A compound according to claim 1 of formula (VII) or a pharmaceutically acceptable salt thereof:

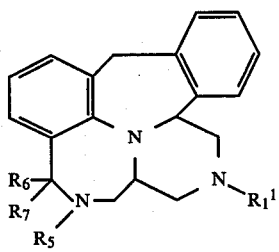

(VII)

wherein R₁¹, R₅, R₆ and R₇ are as defined in claim 2.

7. A compound according to claim 6 of formula (VIII) or a pharmaceutically acceptable salt thereof:

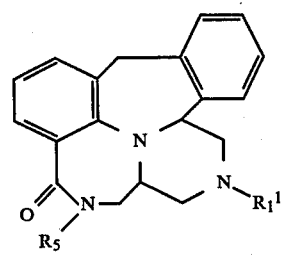

(VIII)

wherein R₁¹ and R₅ are as defined in claim 2.

8. 13-Methyl-1,2,7,11b,12,13,14,14a-octahydro-3H-2,13,14b-triaza-tribenzo[b,ef,kl]heptalen-3-one.

9. A compound selected from the group consisting of:
13-Methyl-1,2,7,11b,12,13,14,14a-octahydro-3H-3,13,14b-triaza-tribenzo[b,ef,kl]heptalene,
3,13-Dimethyl-1,2,7,11b,12,13,14,14a-octahydro-3H-3,13,14b-triaza-tribenzo[b,ef,kl]heptalene and
3-Acetyl-13-methyl-1,2,7,11b,12,13,14,14a-octahydro-3H-3,13,14b-triaza-tribenzo[b,ef,kl]heptalene.

10. A compound selected from the group consisting of:
13-Methyl-1,2,3,11b,12,13,14,14a-octahydro-7-oxa-3,13,14b-triaza-tribenzo[b,ef,kl]heptalen-2-one,
13-Methyl-1,2,7,11b,12,13,14,14a-octahydro-7-oxa-2,13,14b-triaza-tribenzo[b,ef,kl]heptalen-3-one,
13-Methyl-1,2,3,11b,12,13,14,14a-octahydro-7-thia-3,13,14b-triaza-tribenzo[b,ef,kl]heptalen-2-one,
13-Methyl-1,2,3,11b,12,13,14,14a-octahydro-7-thia-2,13,14b-triaza-tribenzo[b,ef,kl]heptalen-3-one,
13-Methyl-1,2,3,11b,12,13,14,14a-octahydro-7-oxa-3,13,14b-triaza-tribenzo[b,ef,kl]heptalene and
13-Methyl-1,2,3,11b,12,13,14,14a-octahydro-7-oxa-2,13,14b-triaza-tribenzo[b,ef,kl]heptalene.

11. A process for the preparation of a compound according to any one of the claims 1 to 10 comprising the steps of reacting a compound of formula (IX):

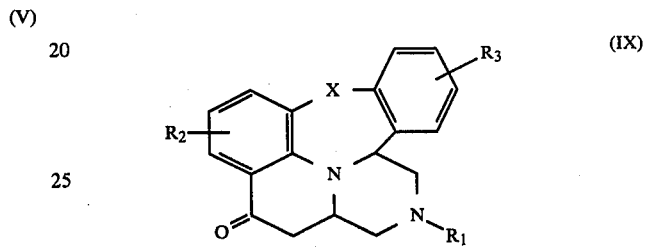

(IX)

with a compound of formula (X):

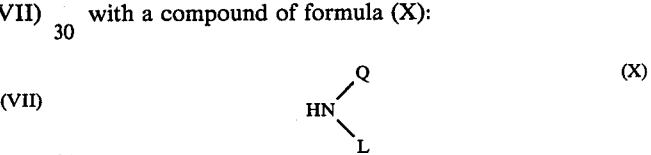

(X)

wherein R₁, R₂, R₃, R₅, R₆ and R₇ are as defined in claim 1, Q is hydrogen and L is a leaving group selected from the group consisting of C₁₋₄ alkoxy, tosyloxy, phosphate and hydroxy (when Y is NR₅) or Q is N₂ and L is absent and treating with an acidic reagent, hydrolysing the resulting intermediate and thereafter optionally reducing an R₆/R₇ oxo group, converting an R₅ hydrogen to other R₅, converting an R₁, R₂ or R₃ group to R₁ or other R₂ or R₃ and/or forming a pharmaceutically acceptable salt thereof.

12. A process for the preparation of a compound according to claim 1 wherein Y is NR₅ and Z is CR₆R₇ comprising the steps of reacting a compound of formula (XI):

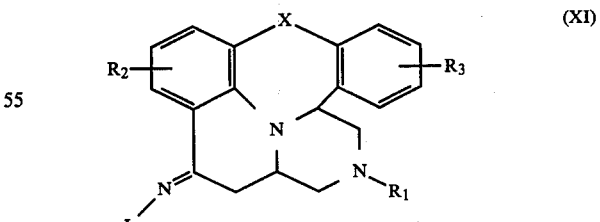

(XI)

wherein R₁, R₂, R₃ and L are as defined in claims 1 and 11 with an acidic reagent, hydrolysing the resulting intermediate and thereafter optionally reducing an R₆/R₇ oxo group, converting an R₅ hydrogen to another R₅, converting an R₁, R₂, or R₃ group to another R₁, R₂ or R₃ and/or forming a pharmaceutically acceptable salt thereof.

13. A pharmaceutical composition for the treatment of CNS disorders in mammals comprising a pharmaceutically effective amount of a compound according to any one of claims 1 to 10 and a pharmaceutically acceptable carrier.

14. A method of treatment of CNS disorder in mammals including humans comprising the administration of a pharmaceutically effective amount of a compound according to any one of the claims 1 to 10 or a pharmaceutically acceptable salt thereof to the sufferer.

* * * * *

UNITED STATES PATENT AND TRADEMARK OFFICE
CERTIFICATE OF CORRECTION

PATENT NO. : 4,469,697
DATED : September 4, 1984
INVENTOR(S) : Derek V. Gardner et al.

It is certified that error appears in the above-identified patent and that said Letters Patent is hereby corrected as shown below:

Column 21, first formula, (E8)   " 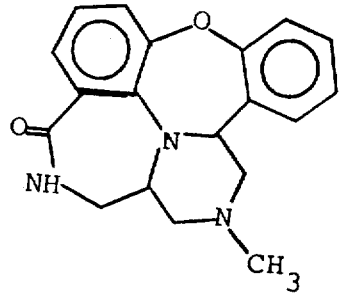 "

should read

-- 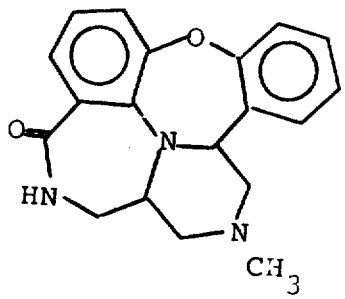 --.

Signed and Sealed this

First Day of October 1985

[SEAL]

Attest:

DONALD J. QUIGG

Attesting Officer

Commissioner of Patents and
Trademarks—Designate